United States Patent [19]

Hakki et al.

[11] Patent Number: 5,569,219
[45] Date of Patent: Oct. 29, 1996

[54] COLLAPSIBLE CATHETER

[76] Inventors: A-Hamid Hakki; Said I. Hakky, both of 8547 Merrimoor Blvd., E., Largo, Fla. 34647-3145

[21] Appl. No.: 306,183

[22] Filed: Sep. 13, 1994

[51] Int. Cl.$^6$ .................................................. A61M 25/00
[52] U.S. Cl. .............................. 604/282; 604/27; 604/30; 604/96; 604/264; 604/327
[58] Field of Search ..................... 604/96, 19, 27, 604/30, 35, 95, 99, 103, 104, 264, 280, 282, 327

[56] References Cited

U.S. PATENT DOCUMENTS

| | | |
|---|---|---|
| 3,894,540 | 7/1975 | Bonner, Jr. . |
| 4,701,162 | 10/1987 | Rosenberg . |
| 4,710,169 | 12/1987 | Christopher ........................ 604/265 X |
| 4,900,314 | 2/1990 | Quackenbush ........................ 604/282 |
| 4,909,787 | 3/1990 | Danforth ........................ 604/282 X |
| 5,098,379 | 3/1992 | Conway et al. . |
| 5,269,755 | 12/1993 | Bodicky . |
| 5,269,770 | 12/1993 | Conway et al. . |
| 5,338,295 | 8/1994 | Cornelius et al. ........................ 604/96 |
| 5,370,899 | 12/1994 | Conway et al. ........................ 604/96 X |
| 5,385,548 | 1/1995 | Williams et al. ........................ 604/96 |
| 5,466,222 | 11/1995 | Ressemonn et al. ........................ 604/96 |
| 5,472,418 | 12/1995 | Palestrant ........................ 604/43 |

*Primary Examiner*—Corrine M. McDermott
*Assistant Examiner*—N. Kent Gring
*Attorney, Agent, or Firm*—John Lezdey and Associates

[57] ABSTRACT

A collapsible catheter is provided for use with an inflatable stiffening or reinforcing member which is capable of being inflated with fluid. The catheter comprises a collapsible hollow elastomeric tube which is open at the proximal end. The distal end portion has at least one aperture. A valve is provided which is at the open end of the elastomeric tube. The valve permits access to inflate the stiffening member. The catheter can be used for draining and aspirating urinary tract or draining or feeding the gastro-intestinal tract.

30 Claims, 4 Drawing Sheets

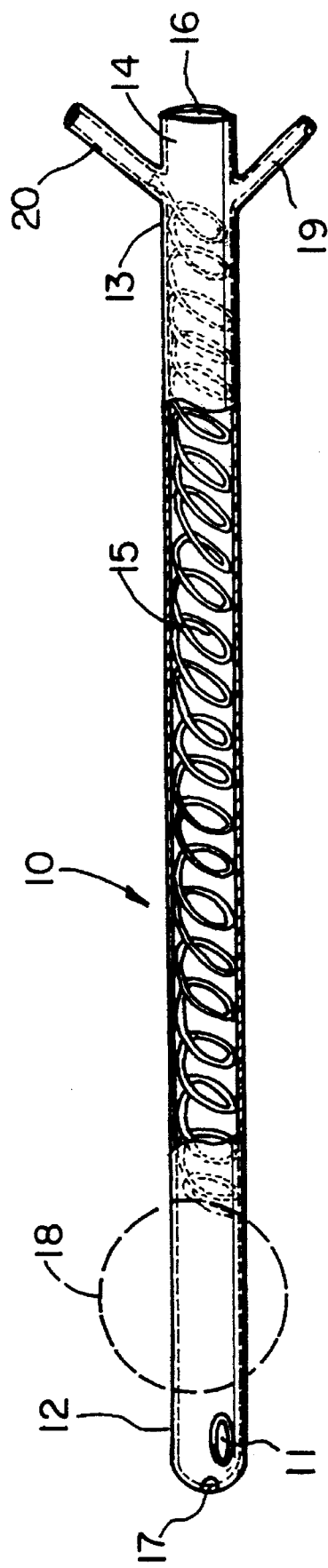
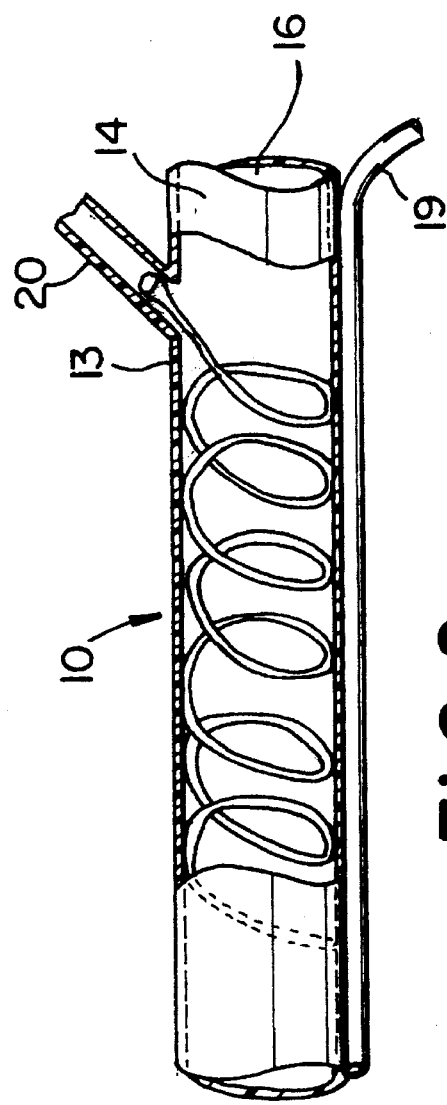

COLLAPSIBLE CATHETER

FIELD OF THE INVENTION

The present invention relates to a surgical device and method for draining or feeding a biological system and in particular a collapsible indwelling catheter is provided for draining or aspirating the urinary bladder and a collapsible naso-gastric tube is provided for draining or feeding the stomach.

BACKGROUND OF THE INVENTION

A urinary bladder tube is used on patients who are unable to urinate. There are many causes of the inability to urinate. Frequently, surgery or other invasive procedures produce such an effect. Generally, the origin of such a condition differs with age and gender. For example, the inability to urinate in men is commonly caused by a blockage of the urethra passageway by an enlargening prostate. In females, the condition may occur after delivery of a baby. And, in small children, a congenital abnormality obstructing the bladder neck or urethra can produce the condition.

After major surgery, it is advantageous to continuously drain the bladder. Continuous drainage of the bladder is also preferred where medical conditions dictate the necessity of monitoring a patient's urine output. It is well known that close measurement of urine output provides a direct correlation to kidney functions and careful monitoring allows one to identify and prevent kidney failure.

It is important to drain the bladder by an indwelling catheter after prostate or bladder surgery. An indwelling Foley type catheter is usually the catheter of choice. U.S. Pat. No. 5,300,022 to Klapper et al and incorporated herein, shows an improvement over the Foley catheter by providing a second lumen for continuous delivery of a sterile irrigating solution directly into the bladder, and preventing any mixture with the main drainage lumen, thus avoiding any reintroduction of harmful bacteria into the bladder during irrigation.

U.S. Pat. No. 4,701,162 issued to Rosenberg and incorporated herein, shows a Foley catheter with two lumens, one for drainage and one for inflation of the balloon. Having separate lumens for drainage and inflation is common in the prior art. U.S. Pat. No. 5,098,379, which is incorporated herein by reference, discloses a Foley catheter having a balloon portion and a lubricated resilient sleeve. U.S. Pat. No. 5,269,770, which is incorporated herein by reference, shows a dual lumen system and balloon Foley catheter for releasing a bactericidal agent. Similarly, U.S. Pat. No. 5,269,755 which is incorporated therein by reference, shows a Foley urinary catheter with a dual membrane delivery system that allows bactericidal agents to diffuse into the urinary tract.

One thing is clear in the prior art of Foley urinary catheters: none of them teach a collapsible device.

An indwelling catheter drains the bladder and diverts the urine from the wound. Moreover, the bladder can be either continuously irrigated with a three way foley catheter or hand irrigated at discrete moments when desired. In the three way catheter, one port used is connected to a large fluid reservoir and the other port is used for drainage of the returned fluid. The speed of irrigation can be controlled by different mechanisms or different pumps.

In certain patients the bladder must be drained for many years, as in patients with spinal cord lesions. If the bladder is not drained, the pressure inside it will build up and obstruct the kidneys. Continuous kidney obstruction could end in renal failure and death in only a few weeks. Furthermore, the catheter is used to clear blockages and constrictions of the urinary tract.

Therefore, the use of indwelling catheter is very important and could be life saving.

However, there are many serious draw backs to the stiff indwelling catheter. First, it is painful and certain patients cannot tolerate the catheter. Second, a stiff hollow indwelling catheter invites micro-organisms to invade the bladder and kidneys which may cause a serious infection. Third, for patients who are unable to tolerate the stiff catheter, a hole in the bladder must be created to drain the bladder directly through the anterior abdominal wall. This is a serious procedure and exposes the patient to unnecessary risks of other complications.

Thus, it would be ideal if a Foley catheter was stiff enough to be introduced, but collapsed after insertion. The urethra is naturally in a state of collapse at rest. The present invention will mimic the urethra's physiological status. The pain or discomfort from an indwelling catheter will be reduced. In addition, the incidence of bladder or kidney infection is minimized.

A naso-gastric tube is currently used to drain or feed a stomach and is necessary after almost any abdominal or bowel surgery. Abdominal or bowel surgery will put the entire gastro-intestinal tract into a state of shock for a period ranging from one day to several days. During this period of shock, the entire gastro-intestinal tract will go into a state of paralysis, namely paralytic ileus. If left unchecked, paralytic ileus could lead to death. But, removing the stomach content with a naso-gastric tube allows the stomach and bowel to recover from their state of paralysis.

Stomach tubes are life saving devices. The stomach, bowel, gall bladder and pancreas produce more than ten liters of secretions per day. When in a state of paralysis, the stomach and bowel fill up with these secretions. Unless drained, the stomach and bowel will distend by at least ten liters per day. It is known in the arts that draining the stomach content will collapse the stomach and decrease acid secretion. This in turn will decrease the alkaline secretions from the bowel, gall bladder and pancreas. Decreasing the secretions conserves the use of the body's immune system, namely, important electrolytes and enzymes are saved for other uses. Moreover, collapsing the gastro-intestinal tract speedens recovery from paralytic ileus. It is known in the arts that a patient will likely die within a few days if paralytic ileus is not treated. Since the nineteenth century, stomach tubes have been used after abdominal or bowel surgery to preserve life until the gastro-intestinal tract recovers.

In addition, a naso-gastric tube is necessary for feeding some debilitated patients. These patients are either in a state of coma or are unable to swallow. The naso-gastric tubes are left in as long as needed. The period for such tube feeding is often a few days or weeks, but it may extend to months and even indefinitely for longterm comatose patients. Furthermore, the tube may be used to clear blockages or restrictions of the gastro-intestinal tract.

And like the prior art for urinary catheters, one thing may be gleaned from the prior art for naso-gastric tubes: none of them teach a collapsible device.

Therefore, the use of naso-gastric tubes to drain or feed the stomach of a patient is very important and often life saving.

However, there are serious draw backs to today's naso-gastric tube. First, the tubes are stiff and therefore very uncomfortable. In fact, they are sometimes so uncomfortable that a patient is not able to tolerate it.

Second, the stiffness of today's naso-gastric tubes causes complications by allowing some of the stomach secretions to move up and down the esophagus during the increase or decrease in the intra-abdominal pressure. The strong esophageal circular muscle sphincter, located at the junction of the stomach and esophagus, usually prevents the movement of acid up and down the esophagus. However, the stiff tube restricts the action of this powerful constricting sphincter and thus allows acid to move up and down the esophagus.

Third, the stiffness of the tube can be a source of infection.

Fourth, when a patient cannot tolerate a naso-gastric tube, the nose, mouth and esophagus must be bypassed by making a hole directly into the stomach. This is a serious procedure and brings more risk to the patient because making a hole in the stomach can cause digestion of the skin.

Thus, it would be ideal if a naso-gastric tube was stiff enough to be introduced into the stomach, but then collapses after insertion. That is what the present invention teaches. The esophagus is naturally in a state of collapse at all times except when food is swallowed or vomited. During eating, the esophagus contracts to propagate swallowed food down and into the stomach. During vomiting, the esophagus reverses the propagation contraction to project the food up and out of the stomach. The present invention will mimic the esophagus's physiological status. The pain or discomfort from a stiff tube will be minimized. In addition, the risk of infection or other complications will be reduced.

SUMMARY OF THE INVENTION

The present invention relates to a catheter for insertion into a patient which is aimed at reducing the discomfiture experienced with conventional indwelling catheters. The catheter of the invention comprises at least a partially collapsible elongated elastomeric tube which is open at a proximal end and has at least one opening at the distal end. A valve means is provided at the proximal end of the tube. The tube is provided with a means for at least partially stiffening or partially collapsing the tube when inserted into the patient.

Advantageously, the means for partially stiffening or collapsing the tube is a balloon means. The balloon means may be within the tube or along its periphery. Preferably when the balloon means is within the tube, it is in the form of a spiral non-distensible hollow tube.

In accordance with one embodiment of the present invention, there is provided a device and method for draining and aspirating the urinary system using a collapsible hollow elastomeric catheter tube. In the device, the tube is thin enough to keep it in a state of collapse at rest. The collapsible tube is open at one end, that is the proximal end and has at least one aperture or distal end at the other end. The open end has a valve which allows passage into and out of the tube.

There are one or more holes, preferably two to three, at the distal end of the tube, which is the end that connects to the bladder. A circular hollow tube can be used to reinforce the open end of the catheter tube, which is the end that connects to a calibrated urine bag. The reinforcement prevents collapse of the open end and facilitates the insertion of the tube connected to the urine bag. The tube may also be stiffened or reinforced by straight or spiral non-distensible hollow balloon means along the entire length of the tube. This balloon can be within the tube or along its periphery and can be at least partially stiffened or expanded. Preferably, the balloons means connects to a valve system at the open end.

The valve system can form the reinforcing member at the tube opening. Moreover, the valve member can comprise an opening for allowing the tip of a syringe to enter or remove fluids to be injected or aspirated in the hollow tube or balloon means.

The balloon member is attached to the outside of said tube or forms a part of its periphery or is entirely within the tube. The balloon can be inflated to prevent the hollow tube from slipping out of the urinary bladder. A small hollow tube preferably connects the balloon to a valve system located near the open end.

In a three way injection system, an extra hollow tube can be added to the proximal end of the catheter and connected to a reservoir for irrigation. This tube does not need to be reinforced with the balloon means.

In addition, a small aperture can be located at the tip of the catheter tube to allow the passage through the catheter of a much smaller guide wire, guide tube or a filiform.

A method is also provided for irrigating and aspirating the urinary tract using a device as the present invention describes herein.

Another embodiment of the invention relates to a device and method for draining and feeding the stomach using a collapsible hollow elastomeric tube. In this device, the tube is thin enough to keep it in a state of collapse at all times except when filled with draining or feeding fluid.

The collapsible tube is reinforced by a straight spiral non-distensible hollow tube along the entire length of the tube. The proximal end of the device is further reinforced with a valve means or circular hollow tube. The open end is soft and transparent and is made out of rubber or rubber-like materials. The distal end which connects to the stomach, can be rigid and made by telescoping two hollow tubes together. One or more side holes are provided in the inner and outer tubes to permit gastric secretions.

The device connects to a valve system at the proximal end which may be connected to a suction pump or feeding tube. Suction at the proximal end is applied only to the inner tube. A radio-opaque line is preferably incorporated along the entire length on the collapsible naso-gastric tube to permit visualization of the position of the device.

The present invention further provides a method for draining or feeding a gastro-intestinal tract using the device described herein.

OBJECT OF THE INVENTION

Accordingly, it is the general object of this invention to provide a collapsible catheter that mimics the urethra in every respect, thus overcoming the disadvantages of the prior arts.

It is a further object of the invention to provide a catheter and method of aspirating the bladder after surgery which can be used with less discomfiture to the patient.

It is a further object of this invention to provide a catheter and method of irrigating the bladder for certain urological conditions.

It is a further object of this invention to provide a catheter that advantageously can be at least partially stiffened or flaccid when desired, thus minimizing the incidence of infection and reducing the pain or discomfort the patient experiences during the period that the catheter is left indwelling.

It is a further object of this invention to provide a hole at the tip of the catheter to provide a port for a guide wire or tube or a filiform to be threaded onto the catheter when desired.

It is another general object of this invention to provide a collapsible catheter that mimics the esophagus in every respect, thus overcoming the disadvantages of the prior arts.

It is a further object of this invention to provide a catheter and method of aspirating the stomach after surgery.

It is a further object of this invention to provide a collapsible catheter and a method of feeding debilitated patients who cannot swallow.

It is a further object of this invention to provide a collapsible catheter that advantageously can be stiff or flaccid when desired, thus minimizing the incidence of infection and reducing the pain or discomfort the patient experiences during the period when the tube is left indwelling.

It is a further object of this invention to provide a collapsible catheter that can be used as sump drainage, that is, a catheter that activates when the stomach starts secreting.

It is yet a further object of this invention to provide a radio-opaque line incorporated in the wall of the collapsible hollow naso-gastric tube that can be used as a marker to identify the position of the tube.

BRIEF DESCRIPTION OF THE DRAWINGS

FIG. 1 is a horizontal view of the collapsible urethral catheter.

FIG. 2 is a cross-section of the collapsible urethral catheter.

DESCRIPTION OF THE PREFERRED EMBODIMENTS

Figure 4:
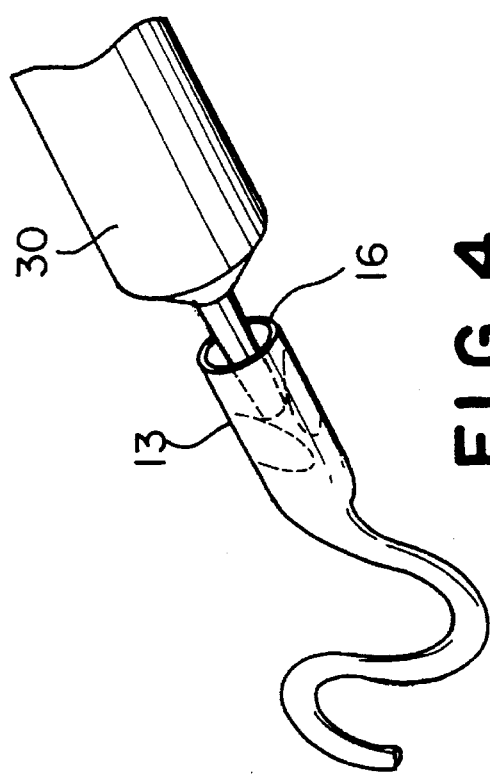
FIG. 4 is a cross-section of the collapsed membrane valve that is distorted after insertion with a syringe.

Although specific terms are used in the following description for the sake of clarity, these terms are intended to refer only to the particular structure of the invention selected for illustration in the drawings and are not intended to define or limit the scope of the invention.

A horizontal view of the collapsible urethral catheter is shown in FIG. 1. The collapsible hollow elastomeric catheter tube 10 is approximately ten to twenty-five millimeters in diameter, thirty to thirty-five centimeters in length, and one tenth of a millimeter in thickness. The tube must be thin enough to keep it in a collapsed state at all times. There are one or more holes 11, preferably two or three, located at the distal end 12 of tube which is the end that connects to the bladder. The holes 11 are advantageously six to eight millimeters in diameter. A small hole 17 is placed at the closed tip 12 of the catheter 10 for use in situations which require the passage of the catheter along a much smaller guide wire or tube or a filiform which is a very small diameter tube.

The open end 13 of the tube 10 is the end that connects to a calibrated urine bag. This end can be reinforced with a circular hollow tube 14 or a valve to prevent collapse of the open end and facilitate the insertion of the tube connected to the urine bag. Advantageously, a collapsible Foley type catheter tube is employed. A spiral non-distensible hollow tube 15 may be employed to partially or fully stiffen or reinforce the catheter tube along its entire length. The spiral non-distensible hollow tube 15 passes around the edges of the multiple holes 11 at the closed end 12 and can reinforce the catheter 10 by using a fluid to prevent any collapse. The spiral non-distensible hollow tube 15 is connected to a valve system 16, 20 at the proximal end 13.

The valve system 16 may be one, two or three ways. FIG. 1 shows a two way valve system 16. A balloon member 18 is attached to the periphery of the catheter. The balloon 18 is at least partially inflated to prevent the catheter 10 from slipping out of the urinary bladder. The balloon 18 is attached to the outside of the catheter 10 and is connected to a small hollow tube of the valve system 16, 19 located near the proximal end 13. The balloon can be filled with approximately thirty cubic centimeters of air or fluid. When inflated, the balloon can fully or partially support the sides of the tube.

Figure 6:
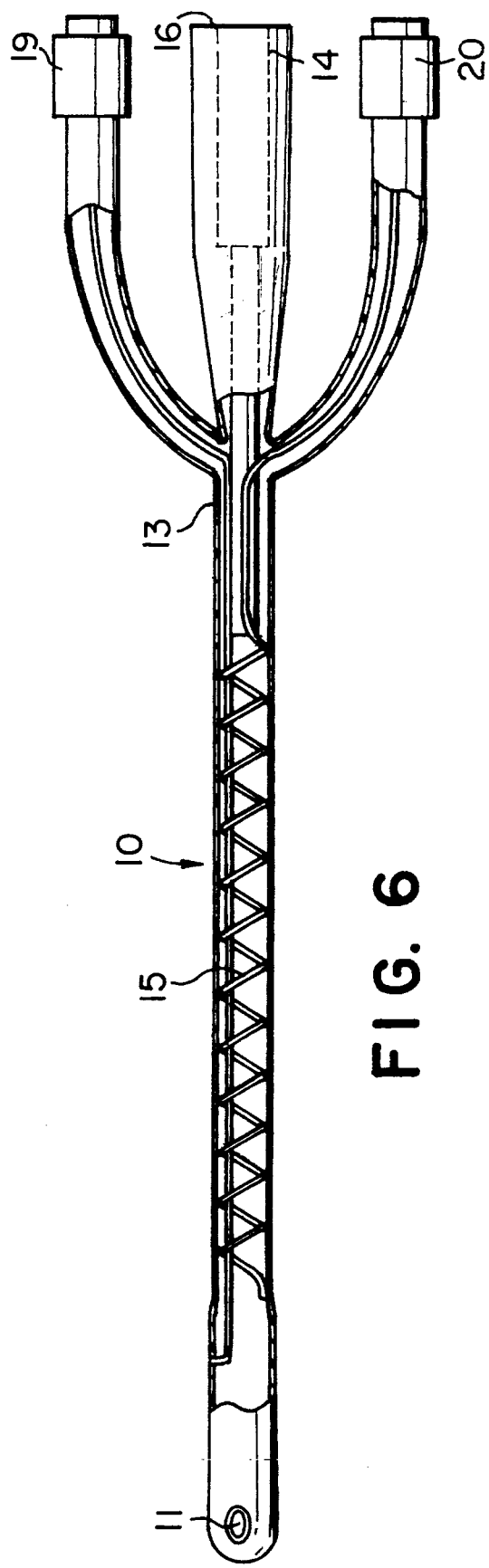
FIG. 6 is a schematic of the two way urethral catheter.

FIG. 6 is a schematic of the present invention utilizing a Foley type collapsible hollow catheter tube 10 and a two way valve system 16. The valve system 16 is located near the proximal or open end 13. One portion 19 of the valve system 16 connects to a straight balloon 18 while the other portion 20 connects to a spiral non-distensible hollow tube or balloon 15 that can reinforce the entire catheter tube 10. The catheter tube 10 is also reinforced with a valve or a hollow tube 14 at the open end 13. One or more holes 11 are provided at the distal end 12 for fluid drainage. The schematic also shows the various points along the catheter tube where the components of the invention are cemented or joined together.

FIG. 2 illustrates a cross-section of the collapsible urethral catheter 10 and shows in detail the distal or open end 13 of the catheter, the valve 16, 19 connected to a hollow tube 14 which then connects to the balloon 18, and the valves 16, 20 are connected to the spiral non-distensible balloon 15.

Figure 3:
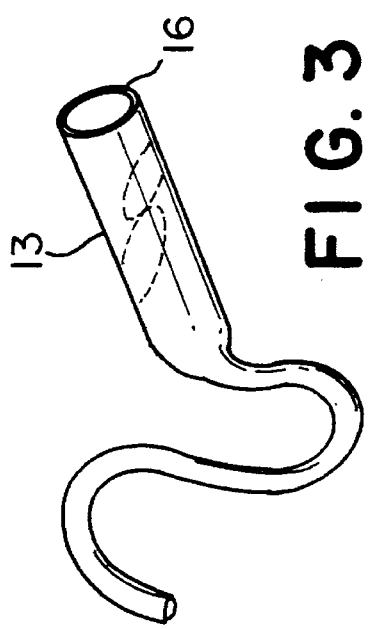
FIG. 3 is a cross-section of the collapsed membrane valve before insertion with a syringe.

The spiral non-distensible balloon 15 connects to the valve system 16 at the end 13. The valve system 16 is illustrated in FIGS. 3 and 4. FIG. 3 shows in detail the valve system 16 at the open end 13 in a collapsed state, while FIG. 4 shows the same valve system 16 when it is distorted due to the insertion of a syringe 30. Inserting the syringe 30 into the valve port 31 distorts the membrane and permits the entry or removal of the fluids to be injected or aspirated in the spiral non-distensible hollow tube or balloon 15.

Figure 5:
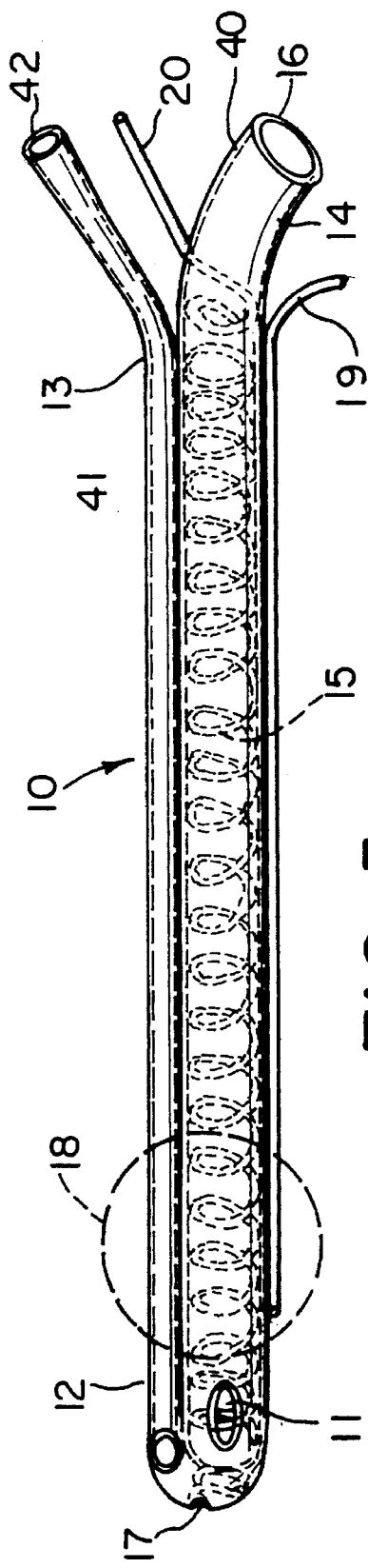
FIG. 5 is a horizontal view of the three way urethral catheter.

A three way valve system 40 is illustrated in FIG. 5. In this embodiment of the invention, an extra hollow tube 41 is added to the catheter 10 and connected to a reservoir of fluid for irrigation. This tube 41 does not need to be reinforced with the spiral non-distensible balloon and ends at a valve 42 near the open end 13 of the catheter 10.

In the method for draining the urinary bladder, the spiral hollow non-distensible balloon is inflated until the entire urethral catheter becomes stiff enough for passage. The stiffened urethral catheter is well lubricated and passed urethrally into the bladder. Once the urethral catheter is in position, as noted by the return of urine, the balloon at the distal end of the catheter is inflated by placing the tip of a syringe in the valve, thus distorting the valve membrane at the open end of the catheter. After the catheter is secured in the urinary bladder, the fluid in the spiral tube is withdrawn, which deflates the indwelling urethral catheter to the collapsed status. The proximal end is connected to a calibrated urine bag furnishing a close system of drainage.

The present invention will mimic the physiological status of the urethra in every respect. In the event of the three way urethral catheter, the fluid will distend the hollow non-reinforced tube when the fluid is turned on. If the fluid is turned off, the infusion or irrigating hollow tube will collapse.

In certain difficult cases, it is customary to first pass a guide tube, guide wire or a filiform (very small diameter tube) into the bladder. The spiral non-distensible tube or balloon is then injected with fluid until the catheter is stiff enough to be threaded along this guide into the bladder. The balloon of the urethral catheter is then inflated with five to ten cubic centimeters of fluid to prevent the catheter from slipping out of the bladder. The non-distensible spiral tube or balloon is then deflated in the manner just described.

Figure 7:
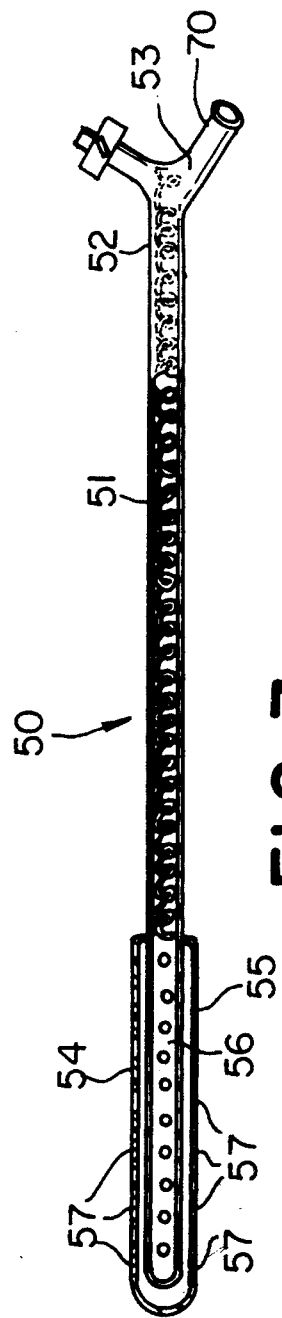
FIG. 7 is a horizontal view of the collapsible naso-gastric tube.

FIG. 7 presents a horizontal view of the collapsible naso-gastric catheter tube. The collapsible hollow elastomeric naso-gastric tube 50 is approximately ten to fifteen millimeters in diameter, one hundred and ten centimeters in length, and a tenth of a millimeter in thickness. The collapsible tube must be thin enough to keep it in a collapsed state when not filled with draining or feeding fluid. Preferably, the collapsible elastomeric tube is made out of silicone or latex.

The collapsible naso-gastric tube 50 may be reinforced with a spiral non-distensible hollow tube 51 along the entire length of the device. Inflating the spiral non-distensible hollow tube 51 with water will stiffen the naso-gastric tube 50.

The proximal or open end 52 of the collapsible naso-gastric tube 50 is connected to a suction pump or feeding bottle. The open end 52 is reinforced with a hollow tube 53 to prevent the collapse of the open end 52 and facilitate the insertion of the tube connections.

The closed end 54 of the collapsible naso-gastric tube 50 is approximately fifteen centimeters long, rigid, and is made by telescoping two hollow fifteen centimeter tubes together 55, 56. The remaining part of the naso-gastric tube is made out of a soft rubber type compound that is transparent and approximately ninety-five centimeters long. The distal end 54 connects to the body of the patient either nasally or orally. The principle of sump suction controls as suction at the open end 52 is applied only to the inner tube 56. The inner 56 and outer 55 tubes have one or more side holes 57 to permit gastric secretions. A sump system of drainage is provided to prevent stomach mucosa from adhering to the holes 57 at the closed end 54.

Figure 8:
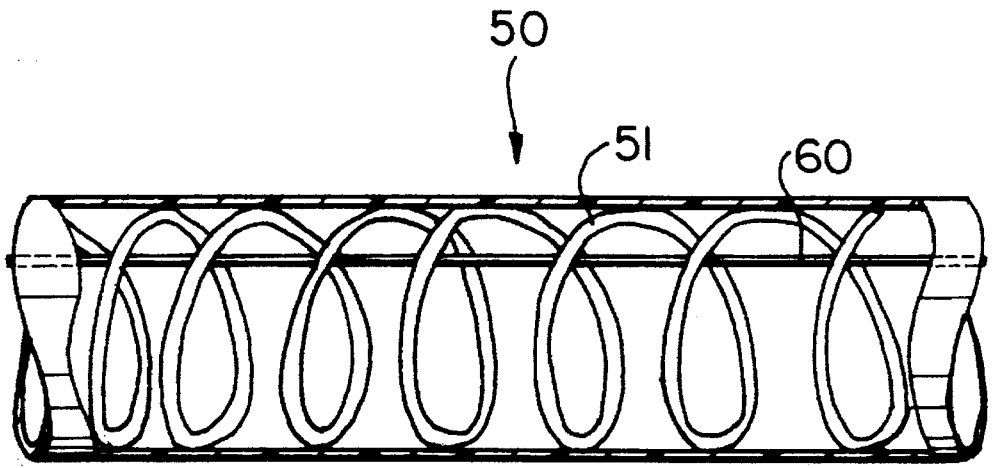
FIG. 8 is a cross-section of the collapsible naso-gastric tube.

FIG. 8 illustrates a cross-section of the collapsible naso-gastric tube 50 and shows in detail the spiral non-distensible hollow tube 51. Also shown is a radio-opaque line 60 which is incorporated along the entire length of the collapsible naso-gastric tube 50 to allow visualization of its position by radiological means during the use of the device.

Figure 9:
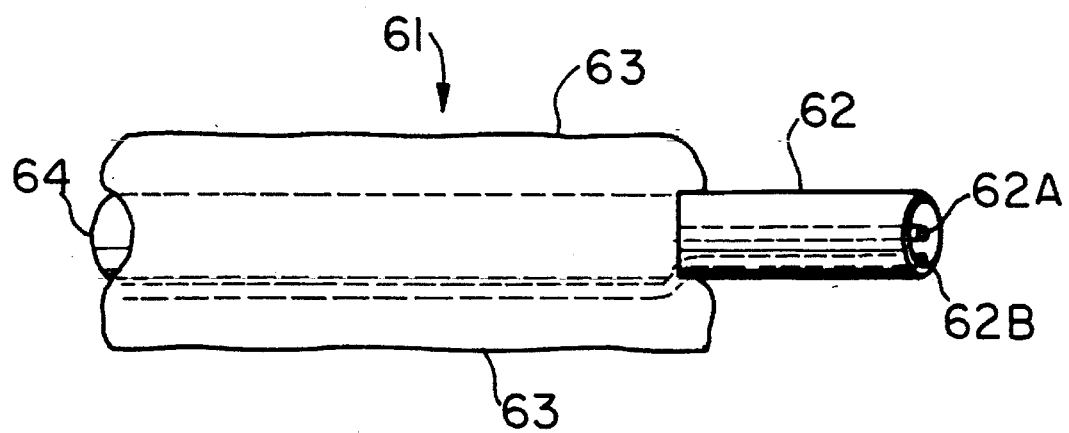
FIG. 9 is a side elevational view of a catheter with straight stiffening means.

FIG. 9 illustrates the catheter 61 which can be partially or fully stiffened or collapsed by means of balloon 63 around its periphery. Catheter 61 is provided with a two way valve 62 having an opening 62A which permits a syringe access to the interior of the catheter to add or drain fluid. Opening 62B provides an access to the balloons 63 with a syringe so as to collapse or inflate the tip or distal end of the catheter can be used either to drain or feed into a body part a fluid.

The present invention also teaches a method for draining or feeding the gastro-intestinal tract using the collapsible naso-gastric tube described herein. The spiral hollow non-distensible tube is inflated until the entire collapsible naso-gastric tube becomes stiff enough for passage. The stiffened collapsible naso-gastric tube is lubricated and passed nasally or orally into the esophagus, and then the stomach. The position in the stomach can be checked by the acidity of the returned fluid or by means of radiological imaging. Once the collapsible naso-gastric tube is in position, the fluid in the spiral tube is withdrawn which deflates the naso-gastric tube to a collapsed state. The open end of the device is connected to a suction pump or a feeding bottle depending on the reason for the insertion of the collapsible naso-gastric tube. The present invention will mimic the physiological status of the esophagus in every respect.

In the event of feeding, the feeding fluid will distend the collapsible naso-gastric tube during the passage of the bolus fluid. The collapsible tube remains collapsed when no fluid is injected and is more comfortable to the patient. Also, this allows the powerful sphincter at the junction of the stomach and esophagus to continue to contract, thus preventing the feeding fluid or acid of the stomach from regurgitating up the esophagus. This is essential because regurgitation of feed fluid into the esophagus carries the fatal risk of aspirating the feed fluid into the lungs of debilitated patients or those who cannot swallow.

In the event that the naso-gastric tube is used for draining the stomach content after abdominal or bowel surgery, the spiral hollow tube is filled with fluid until the naso-gastric tube becomes stiff enough for passage. The collapsible naso-gastric tube is lubricated and inserted nasally or orally down the esophagus and into the stomach. Again, the position of the naso-gastric tube is confirmed by the acid return fluid or radiological means. The fluid in the spiral tube is drained, thus collapsing the naso-gastric tube. The open end of the collapsible naso-gastric tube is connected to a suction pump. The sump drain action prevents the gastric mucosa from plugging the small drainage side holes at the closed end of the collapsible naso-gastric tube.

Although the invention has been described with a certain degree of particularity, it is understood that the present disclosure has been made only by way of example and that numerous changes in the details of construction and the combination and arrangement of parts may be resorted to without departing from the spirit and scope of the invention.

What is claimed:

1. A catheter for insertion into a patient, said catheter comprising:
   a) at least a partially collapsible elongated elastomeric tube wherein the tube is thin enough to remain in a state of collapse at all times and which is open at a proximal end and substantially closed at a distal end, the distal end of said tube having at least one opening;
   b) valve means at the proximal end of said elastomeric tube; and
   c) actuation balloon means along said tube for at least partially collapsing or partially stiffening said elastomeric tube when inserted in the patient.

2. The catheter of claim 1 wherein said balloon means is along the periphery of said elastomeric tube.

3. The catheter of claim 1 wherein said balloon means extends longitudinally substantially along the length of said elastomeric tube.

4. The catheter of claim 1 wherein said balloon means is within said elastomeric tube.

5. The catheter of claim 1 wherein said balloon means comprises a spiral non-distensible hollow tube.

6. The catheter of claim 1 wherein said elastomeric tube comprises latex or silicone.

7. The catheter of claim 6 wherein said elastomeric tube comprises silicone.

8. The catheter of claim 6 wherein said elastomeric tube comprises latex.

9. The catheter of claim 1 wherein said catheter comprises a Foley type catheter.

10. The catheter of claim 1 wherein said catheter has an aperture about the distal end for use with a guide wire, guide tube or filiform.

11. The catheter of claim 10 wherein said apertures at the distal end are approximately six to eight millimeters in diameter.

12. The catheter of claim 1 wherein said elastomeric tube is reinforced along the inside with a hollow tube at the proximal end of said elastomeric tube.

13. The catheter of claim 1 wherein said means balloon for stiffening or collapsing comprises a spiral non-distensible hollow tube substantially along the entire inner length of said elastomeric tube.

14. The catheter of claim 1 wherein said means for stiffening or collapsing comprises said balloon means along the periphery of said elastomeric tube.

15. The catheter of claim 14 wherein said balloon means is associated with said valve means so that said valve means controls entry of air or fluid to inflate said balloon means and removal of air or fluid to deflate said balloon means.

16. The catheter of claim 14 comprising a spiral non-distensible hollow tube within said elastomeric tube and an urine bag connected to the longitudinal axis of said elastomeric tube, wherein said valve means includes a two way valve system near the proximal end of said elastomeric tube, one direction of said valve system connects to said spiral non-distensible hollow tube, the second direction of said valve connects to said balloon means.

17. The catheter of claim 1 wherein said valve means comprises a three way valve wherein one direction of said valve is connected to a hollow tube that holds a reservoir of fluid for irrigation.

18. The catheter of claim 1 for draining an urinary bladder wherein said catheter is approximately ten to twenty-five millimeters in diameter, thirty to thirty-five centimeters in length, and a tenth of a millimeter in thickness.

19. The catheter of claim 1 for treating a stomach of said patient, wherein said catheter is about ten to fifteen millimeters in diameter, about one hundred and ten centimeters in length, and a tenth of a millimeter in thickness.

20. The catheter of claim 1 wherein said elastomeric tube comprises a pair of telescoping hollow tubes at the distal end for making the distal end of said elastomeric tube stiffer than the remainder of said catheter.

21. The catheter of claim 20 wherein both inner and outer said telescoping hollow tubes have one or more apertures.

22. The catheter of claim 1 further comprising a radio-opaque line along the entire length of said catheter.

23. A method for draining or feeding a stomach of said patient with the catheter of claim 1 comprising the steps of inflating said balloon means for stiffening tube with fluid until said elastomeric tube stiffens, lubricating said catheter, passing said catheter nasally into an esophagus of said patient, then the stomach, locating said position of said catheter with the acidity of returned fluid or a radiological image, distorting said catheter at the open end to permit entry or removal of fluids, and then withdrawing the fluid from said means for stiffening tube to collapse said elastomeric tube.

24. The method of claim 23 for use in feeding said stomach wherein said elastomeric tube is connected to a feeding bottle at the open end, and wherein said elastomeric tube is in a state of collapse except when feeding fluid is introduced which inflates and stiffens said elastomeric tube during the passage of fluid.

25. The method of claim 23 for use in draining said stomach wherein said elastomeric tube is connected to a suction pump at the open end, and wherein said elastomeric tube is in a state of collapse except when draining fluid is introduced which stiffens said elastomeric tube.

26. A collapsible catheter comprising:
   a) a collapsible hollow elastomeric tube which is closed at one end and open at the other end, said elastomeric tube having at least one aperture at the closed end;
   b) a spiral non-distensible hollow tube substantially along the entire inner length of said elastomeric tube, said spiral non-distensible hollow tube stiffening or reinforcing said elastomeric tube when injected with fluid;
   c) valve means connected to said elastomeric tube at the open end of said tube, said valve means having an opening for access to said spiral non-distensible hollow tube;
   d) a balloon member outside of said elastomeric tube and attached thereto; and
   e) actuation means for inflating and deflating said balloon member.

27. A method for irrigating or aspirating a urinary tract of said patient employing the catheter of claim 26 wherein said valve means includes a valve membrane, said method comprising the steps of inflating said spiral non-distensible hollow tube until the entire catheter becomes stiff enough for passage, passing said catheter urethrally with the closed end into a bladder of said patient until the commencement of the flow of urine indicates the proper position of the catheter, placing the tip of a syringe in said valve membrane to distort said membrane at the open end of said catheter so as to cause inflation of said balloon at the closed end of said catheter, withdrawing the fluid in said spiral non-distensible hollow tube so as to deflate said catheter, and closing drainage by connecting the open end of said catheter to a calibrated urine bag.

28. The method of claim 27 wherein fluid partially stiffens said elastomeric tube when the fluid is turned on and said elastomeric tube partially collapses when the fluid is turned off.

29. The method of claim 27 wherein a guide tube or wire or a filiform is passed first into the bladder, then said spiral non-distensible hollow tube is injected with air or fluid until said catheter is stiff enough to be threaded along said guide wire or tube or said filiform into the bladder.

30. The method of claim 29 wherein five to ten cubic centimeters of fluid inflates said balloon of said catheter to secure the catheter in the bladder, and wherein said spiral non-distensible hollow tube is then deflated.

* * * * *